US011517247B2

(12) United States Patent
Mazumder et al.

(10) Patent No.: US 11,517,247 B2
(45) Date of Patent: Dec. 6, 2022

(54) METHOD AND SYSTEM FOR DETECTING PARKINSON'S DISEASE PROGRESSION

(71) Applicant: Tata Consultancy Services Limited, Mumbai (IN)

(72) Inventors: Oishee Mazumder, Kolkata (IN); Rahul Gavas, Bangalore (IN); Aniruddha Sinha, Kolkata (IN)

(73) Assignee: TATA CONSULTANCY SERVICES LIMITED, Mumbai (IN)

(*) Notice: Subject to any disclaimer, the term of this patent is extended or adjusted under 35 U.S.C. 154(b) by 301 days.

(21) Appl. No.: 16/796,972

(22) Filed: Feb. 21, 2020

(65) Prior Publication Data
US 2020/0268306 A1 Aug. 27, 2020

(30) Foreign Application Priority Data
Feb. 22, 2019 (IN) .............................. 201921007036

(51) Int. Cl.
*A61B 5/00* (2006.01)
*A61B 5/103* (2006.01)

(52) U.S. Cl.
CPC .......... *A61B 5/4082* (2013.01); *A61B 5/1038* (2013.01); *A61B 5/4842* (2013.01); *A61B 5/6807* (2013.01); *A61B 5/7278* (2013.01)

(58) Field of Classification Search
CPC ... A61B 5/4082; A61B 5/1038; A61B 5/4842; A61B 5/6807; A61B 5/7278;
(Continued)

(56) References Cited

U.S. PATENT DOCUMENTS

| 2012/0092169 A1* | 4/2012 | Kaiser | G16H 50/20 600/587 |
| 2015/0018664 A1* | 1/2015 | Pereira | G16H 50/20 600/410 |

(Continued)

OTHER PUBLICATIONS

Mariani, B. et al. (Jan. 2013). "On-Shoe Wearable Sensors for Gait and Turning Assessment of Patients With Parkinson's Disease," *IEEE Transactions on Biomedical Engineering*, vol. 60, No. 1; pp. 155-158.
(Continued)

*Primary Examiner* — Devin B Henson
*Assistant Examiner* — Joseph A Tombers
(74) *Attorney, Agent, or Firm* — Finnegan, Henderson, Farabow, Garrett & Dunner LLP

(57) ABSTRACT

This disclosure relates generally to a Parkinson's disease detection system. Parkinson's disease is a neuro-degenerative disorder affecting motor and cognitive functions of subjects. Since symptom manifestation is limited in Parkinson's disease, identifying Parkinson's disease in the early stage is a challenging task. The present disclosure overcomes the limitations of the conventional methods for detecting Parkinson's disease by utilizing a graph theory approach. Here, each pressure sensor attached to an insole corresponding to a plurality of pressure points associated with a foot of the subject is considered as a node of a connectivity graph. The foot dynamics analysis is performed based on a metric known as mediolateral stability index and the mediolateral stability index is calculated by utilizing a betweenness centrality associated with each node of the connectivity graph. Further, the mediolateral stability index is compared with standard values to detect the intensity of the Parkinson's disease.

5 Claims, 11 Drawing Sheets

(58) Field of Classification Search
CPC ............ A61B 2562/0247; A61B 5/112; A61B 5/4023; G16H 50/30; G16H 50/70; G16H 50/20
See application file for complete search history.

(56) References Cited

U.S. PATENT DOCUMENTS

2016/0192862 A1* 7/2016 Merrell .................. A61B 5/112
600/592
2017/0238870 A1 8/2017 Lee et al.

OTHER PUBLICATIONS

Khoury, N. et al. (Jan. 2019). "Data-Driven Based Approach to Aid Parkinson's Disease Diagnosis," *Sensors*, vol. 19, No. 242; pp. 1-27.

* cited by examiner

_US 11,517,247 B2_

METHOD AND SYSTEM FOR DETECTING PARKINSON'S DISEASE PROGRESSION

PRIORITY CLAIM

This U.S. patent application claims priority under 35 U.S.C. § 119 to: India Application No. 201921007036, filed on Feb. 22, 2019. The entire contents of the aforementioned application are incorporated herein by reference.

TECHNICAL FIELD

The disclosure herein generally relates to health monitoring, and, more particularly, to a method and system for detecting Parkinson's disease progression.

BACKGROUND

Parkinson's disease is a neuro-degenerative disorder causing motor and cognitive impairments in subjects. Major motor impairments includes gait impairments like freezing of gait, reshuffled gait, asymmetry in upper limb motion during gait, slowed movement, resting tremor, rigidity and postural instability. Since symptom manifestation is limited in Parkinson's disease, identifying Parkinson's disease in the early stage and monitoring the progression of the Parkinson's disease is a challenging task.

Conventional methods focus either on symptom manifestations of a subject to detect the Parkinson's Disease (PD) or on common gait features of subjects like stride time and swing time to monitor the progression of the PD. Since the gait features are univariate functions, there is a challenge in monitoring the progression of the PD. Further, in early stage of the Parkinson's disease the symptom may not be strong and distinct. Hence, symptom based approaches provide lower accuracy in detection of the disease and hence not a preferred approach for early detection. Recently, existing approaches are analyzing standard gait metrics like stride length that arises due to interaction of the insole pressure points to detect the PD. However, these existing methods provide only gait abnormality analysis, profound only in the advanced stage of the PD. Hence there is a challenge in detecting PD of the subject in early stages.

SUMMARY

Embodiments of the present disclosure present technological improvements as solutions to one or more of the above-mentioned technical problems recognized by the inventors in conventional systems. For example, in one embodiment, a method for detecting Parkinson's disease progression is provided. The method includes receiving, a Vertical Ground Reaction Force (VGRF) data from each of a plurality of pressure sensors attached to an insole. Further, the method includes determining, a stride information for each of the plurality of pressure sensors from the corresponding VGRF data, wherein each of the plurality of pressure sensors correspond to a plurality of pressure points in a foot of the subject, and each pressure point corresponds to a node in a graph. Furthermore, the method includes calculating, a mediolateral stability index from the calculated stride information associated with each node in the graph based on a betweenness centrality associated with each node. Finally, the method includes detecting an intensity of the Parkinson's disease of the subject by comparing the mediolateral stability index with a predetermined value.

In another aspect, a system for detecting Parkinson's disease progression is provided. The system includes an insole with a plurality of pressure sensors, at least one memory comprising programmed instructions, at least one hardware processor operatively coupled to the at least one memory, wherein the at least one hardware processor are capable of executing the programmed instructions stored in the at least one memories; and a gait dynamics analysis unit, wherein the gait dynamics analysis unit is configured to receive, a Vertical Ground Reaction Force (VGRF) data from each of a plurality of pressure sensors attached to an insole. Further, the gait dynamics analysis unit is configured to determine, a stride information for each of the plurality of pressure sensors from the corresponding VGRF data, wherein each of the plurality of pressure sensors correspond to a plurality of pressure points in a foot of the subject, and each pressure point corresponds to a node in a graph. Furthermore, the gait dynamics analysis unit is configured to calculate, a mediolateral stability index from the calculated stride information associated with each node in the graph based on a betweenness centrality associated with each node. Finally, the gait dynamics analysis unit is configured to detect, an intensity of the Parkinson's disease of the subject by comparing the mediolateral stability index with a predetermined value.

In yet another aspect, a computer program product comprising a non-transitory computer-readable medium having embodied therein a computer program for method and system for detecting Parkinson's disease progression, is provided. The computer readable program, when executed on a computing device, causes the computing device to receive, a Vertical Ground Reaction Force (VGRF) data from each of a plurality of pressure sensors attached to an insole. Further, the computer readable program, when executed on a computing device, causes the computing device to determine, a stride information for each of the plurality of pressure sensors from the corresponding VGRF data, wherein each of the plurality of pressure sensors correspond to a plurality of pressure points in a foot of the subject, and each pressure point corresponds to a node in a graph. Furthermore, the computer readable program, when executed on a computing device, causes the computing device to calculate, a mediolateral stability index from the calculated stride information associated with each node in the graph based on a betweenness centrality associated with each node. Finally, the computer readable program, when executed on a computing device, causes the computing device to detect, an intensity of the Parkinson's disease of the subject by comparing the mediolateral stability index with a predetermined value.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
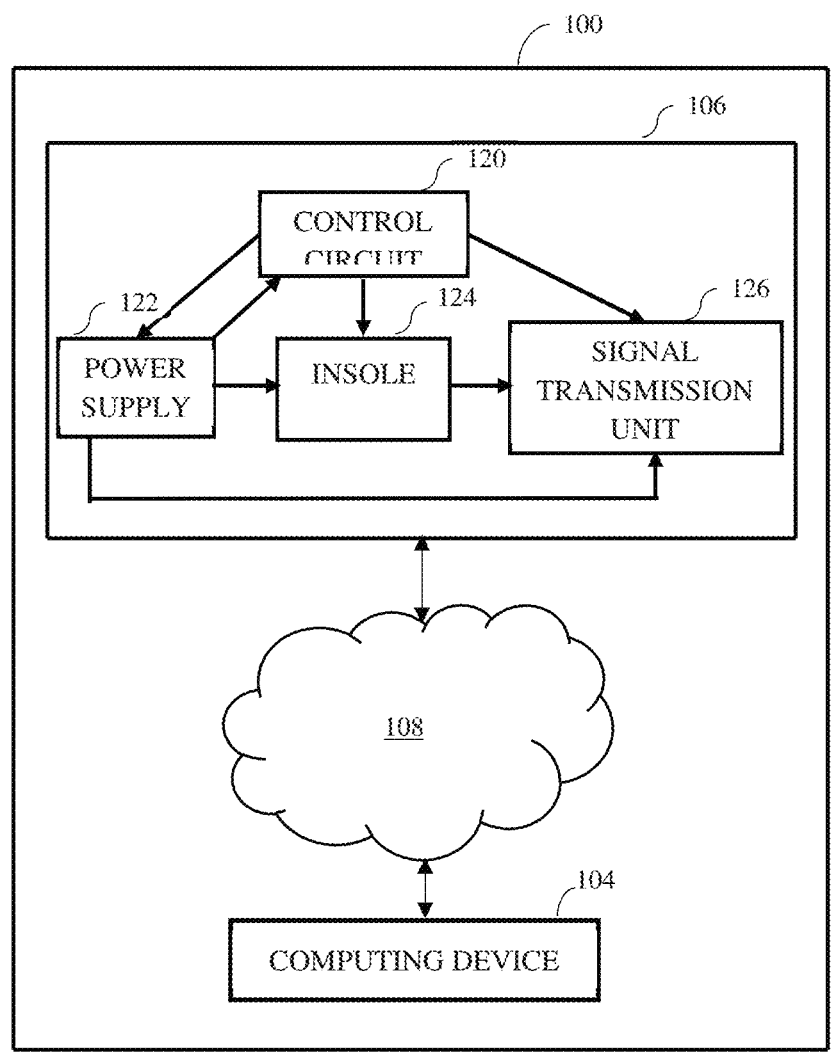
FIG. 1 illustrates an exemplary networking environment for implementing a system for detecting Parkinson's disease progression according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments.

Provided below are definitions of a plurality if terms used herein.

Control subject (CO): A subject not having Parkinson's disease.

Stride information: A stride information refers to a period of time comprising a heel strike phase followed by a toe off phase further back to the heel strike phase. The heel strike phase refers to a gesture of a subject when a foot of the subject makes contact with ground. The toe off phase refers to the gesture when a toe of the subject goes off the ground.

Modularity (M): Modularity is a measure of nodes forming modules and the modules refers to a set of nodes with denser links among them and sparser links with rest of the graph.

Characteristic Path Length (CPL): CPL is an average path length in a connectivity graph, where a path length is defined as the minimum number of edges to be traversed from one node of the connectivity graph to another node.

Clustering Coefficient (CC): Clustering coefficient provides an indication of connectivity of a node with a plurality of neighboring nodes in the connectivity graph.

Embodiments herein provide a method and system for detecting Parkinson's disease progression. The present subject matter overcomes the limitations of the conventional methods for detecting Parkinson's disease progression by utilizing a graph theory approach. Here, the graph theory based approach is utilized to analyze foot dynamics of the subject. A plurality of pressure sensors are attached to an insole corresponding to a plurality of pressure points associated with the foot of the subject. Each pressure point associated with the foot of the subject is considered as a node of a connectivity graph. The foot dynamics analysis is performed based on a metric known as mediolateral stability index and the mediolateral stability index is calculated by utilizing a betweenness centrality associated with each node of the connectivity graph. Further, the mediolateral stability index is compared with standard values to detect the intensity of the Parkinson's disease. An implementation of the method and system for detecting Parkinson's disease progression is described further in detail with reference to FIGS. 1 through 8.

Referring now to the drawings, and more particularly to FIG. 1 through 8, where similar reference characters denote corresponding features consistently throughout the figures, there are shown preferred embodiments and these embodiments are described in the context of the following exemplary system and/or method.

FIG. 1 illustrates an exemplary networking environment for implementing a system for detecting Parkinson's disease progression, according to an example embodiment of the present subject matter. The system 100 for detecting Parkinson's disease progression, hereinafter referred to as the system 100, includes a computing device 104, an insole unit 106 and a network 108. Here the computing device 104 can be one among a variety of computing systems, such as a laptop computer, a desktop computer, a notebook, a workstation, a cloud-based computing device, a router, a network gateway, a sensor gateway, a wifi access point and the like. In one implementation, the system 100 may be implemented in a cloud-based environment. In another implementation, the system 100 can be implemented in a cloud-edge environment and in yet another implementation, the system 100 can be implemented in a cloud-fog environment. The insole unit 108 and the computing device 104 are communicatively coupled through a network 108.

In an embodiment, the network 108 may be a wireless or a wired network, or a combination thereof. In an example, the network 108 can be implemented as a computer network, as one of the different types of networks, such as virtual private network (VPN), intranet, local area network (LAN), wide area network (WAN), the internet, and such. The network 108 may either be a dedicated network or a shared network, which represents an association of the different types of networks that use a variety of protocols, for example, Hypertext Transfer Protocol (HTTP), Transmission Control Protocol/Internet Protocol (TCP/IP), and Wireless Application Protocol (WAP), to communicate with each other. Further, the network 108 may include a variety of network devices, including routers, bridges, servers, computing devices, storage devices. The network devices within the network 108 may interact with the each other through communication links.

In an embodiment, the insole unit 106 includes an insole 124, a signal transmission unit 126, a power supply 122 and a control circuit 120. The insole 124 includes a plurality of pressure sensors and each pressure sensor from the plurality of pressure sensors attached with the insole 124 corresponds to a plurality of pressure points associated with the foot of the subject. Each of the plurality of pressure sensors measures a Vertical Ground Reaction Force (VGRF) data associated with the particular pressure point of the foot. In an embodiment, eight pressure points are identified and hence eight pressure sensors are attached in the insole corresponding to the eight pressure points. In an embodiment, the plurality of pressure sensors may include Ultraflex Computer Dyno Graphy™, Infotronic Inc.™. The signal transmission unit 126 collects a plurality of VGRF data from the plurality of pressure sensors and transmits the plurality of VGRF data to the computing device 104. The power supply 122 supplies power to the plurality of pressure sensors attached to the insole 124, the signal transmission unit 126 and the control circuit 120. The control circuit 120 controls and coordinates a plurality of functions associated with the insole unit 106.

Figure 2:
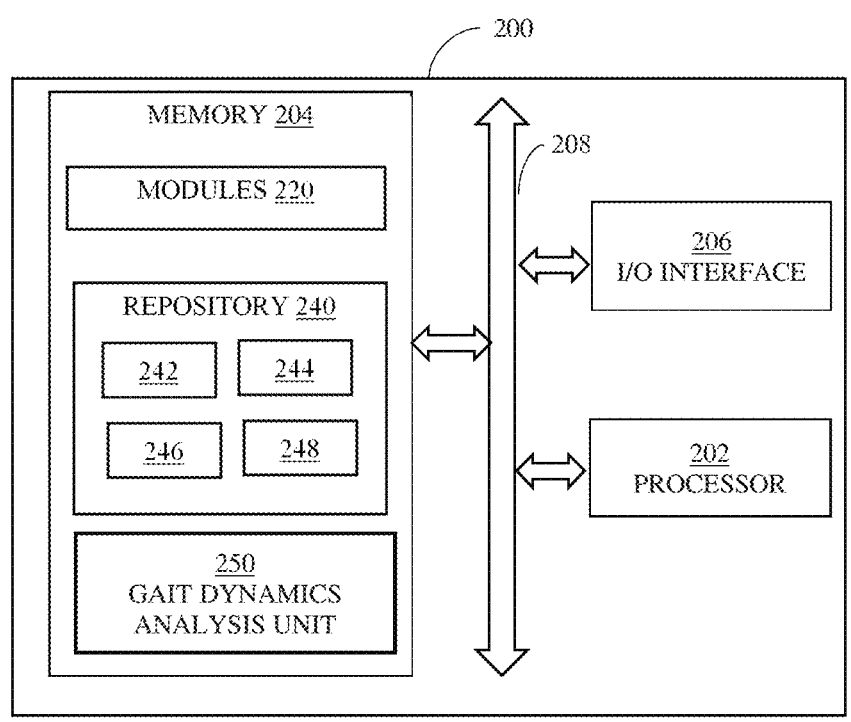
FIG. 2 is a functional block diagram of the system for detecting Parkinson's disease progression according to some embodiments of the present disclosure.

FIG. 2 illustrates a block diagram of a computing device 104, according to some embodiments of the present disclosure. The computing device 104 (hereinafter referred to as system 200) includes or is otherwise in communication with one or more hardware processors such as a processor 202, at least one memory such as a memory 204, an I/O interface 206 and a gait dynamics analysis unit 250. In an embodiment, the gait dynamics analysis unit 250 comprising a stride information calculation module (not shown in FIG. 2), a mediolateral stability index calculation module (not shown in FIG. 2), and a categorization module (not shown in FIG. 2). The processor 202, memory 204, and the I/O interface 206 may be coupled by a system bus such as a system bus 208 or a similar mechanism.

The I/O interface 206 may include a variety of software and hardware interfaces, for example, a web interface, a graphical user interface, and the like. The interfaces 206 may include a variety of software and hardware interfaces, for example, interfaces for peripheral device(s), such as a keyboard, a mouse, an external memory, a camera device, and a printer. Further, the interfaces 206 may enable the system 200 to communicate with other devices, such as web servers and external databases. The interfaces 206 can facilitate multiple communications within a wide variety of networks and protocol types, including wired networks, for example, local area network (LAN), cable, etc., and wireless networks, such as Wireless LAN (WLAN), cellular, or satellite. For the purpose, the interfaces 206 may include one or more ports for connecting a number of computing systems with one another or to another server computer. The I/O interface 206 may include one or more ports for connecting a number of devices to one another or to another server.

The hardware processor 202 may be implemented as one or more microprocessors, microcomputers, microcontrollers, digital signal processors, central processing units, state machines, logic circuitries, and/or any devices that manipulate signals based on operational instructions. Among other capabilities, the hardware processor 202 is configured to fetch and execute computer-readable instructions stored in the memory 204.

The memory 204 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 204 includes a plurality of modules 220 and a repository 240 for storing data processed, received, and generated by one or more of the modules 220 and the gait dynamics analysis unit 250. The modules 220 may include routines, programs, objects, components, data structures, and so on, which perform particular tasks or implement particular abstract data types.

The memory 204 also includes module(s) 220 and a data repository 240. The module(s) 220 include programs or coded instructions that supplement applications or functions performed by the system 100 for detecting Parkinson's disease progression. The modules 220, amongst other things, can include routines, programs, objects, components, and data structures, which perform particular tasks or implement particular abstract data types. The modules 220 may also be used as, signal processor(s), state machine(s), logic circuitries, and/or any other device or component that manipulates signals based on operational instructions. Further, the modules 220 can be used by hardware, by computer-readable instructions executed by a processing unit, or by a combination thereof. The modules 220 can include various sub-modules (not shown). The modules 220 may include computer-readable instructions that supplement applications or functions performed by the system a00 for detecting Parkinson's disease progression.

The data repository 240 may include received set of tasks, a reference database 244, a VGRF database 246 and other data 248. Further, the other data 248 amongst other things, may serve as a repository for storing data that is processed, received, or generated as a result of the execution of one or more modules in the module(s) 220 and the modules associated with the gait dynamics analysis unit 250.

Although the data repository 240 is shown internal to the system 200, it will be noted that, in alternate embodiments, the data repository 240 can also be implemented external to the system 200, where the data repository 240 may be stored within a database (not shown in FIG. 2) communicatively coupled to the system 200. The data contained within such external database may be periodically updated. For example, new data may be added into the database (not shown in FIG. 2) and/or existing data may be modified and/or non-useful data may be deleted from the database (not shown in FIG. 2). In one example, the data may be stored in an external system, such as a Lightweight Directory Access Protocol (LDAP) directory and a Relational Database Management System (RDBMS). In another embodiment, the data stored in the data repository 240 may be distributed between the 200 and the external database.

Figure 3A:
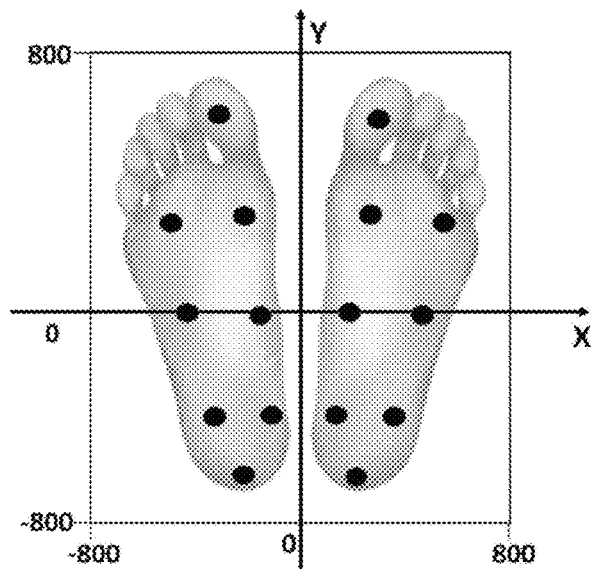
FIG. 3A illustrates an exemplary representation of a plurality of pressure points of a foot corresponding to a plurality of pressure sensors arranged in an insole, in accordance with some embodiments of the present disclosure.

The gait dynamics analysis unit 250 of the system 200 can be configured to receive a Vertical Ground Reaction Force (VGRF) data from each of the plurality of pressure sensors attached with the insole 124. Each of the plurality of pressure sensors measures the VGRF data associated with the particular pressure point of the foot at 100 Hz sampling frequency. Further, the VGRF data is filtered to reduce spurious noise and to suppress raw signal less than 20 N. Further, the VGRF data during the initial 20 seconds of each pressure sensor is discarded. In an embodiment, eight pressure points are identified and eight pressure sensors are attached in the insole corresponding to the eight pressure points. FIG. 3A illustrates an exemplary representation of the plurality of pressure points of the foot corresponding to the plurality of pressure sensors arranged in the insole, in accordance with some embodiments of the present disclosure. Referring to FIG. 3A, the pressure points are selected with reference to an arbitrary reference coordinate system. Here, an arbitrary axis is placed such that a left foot is positioned on positive axis and a right foot is positioned on negative axis. Further, upper half section of the left foot and the right foot are positioned on positive axis and lower half of the left foot and the right foot are positioned on negative axis. In an embodiment, placement of said arbitrary axis is utilized for calculating a center of pressure when the subject is walking. The VGRF data recorded under each foot are normalized in association with body weight of the subject.

Figure 3B:
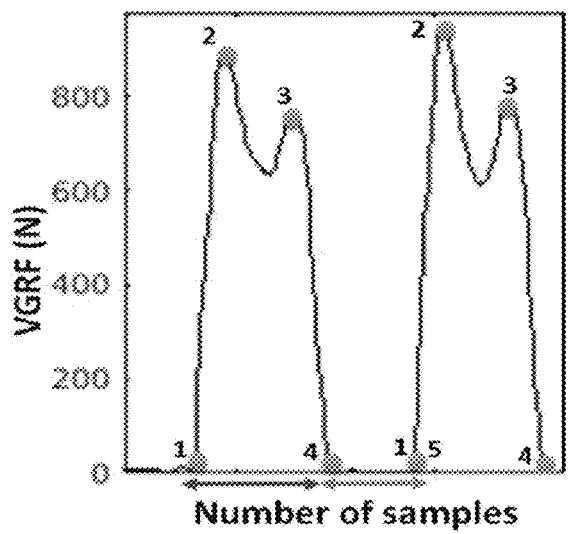
FIG. 3B is an exemplary graph showing Vertical Ground Reaction Force (VGRF) data and corresponding stride information, according to some embodiments of the present disclosure.

Further, the gait dynamics analysis unit 250 of the system 200 can be configured to calculate the stride information from the VGRF data associated with the each of the plurality of pressure sensors. FIG. 3B is an exemplary graph showing the VGRF data and a corresponding stride information, according to some embodiments of the present disclosure. Referring to FIG. 3B, a nature of VGRF of the subject while walking is shown. Here, each cycle includes two peaks, corresponding to the phases of the gait cycle and a single gait cycle is known as stride. A plurality of gait parameters including stride time, velocity, can be calculated from the gait cycle. In an embodiment, the stride information is calculated from the VGRF data by utilizing a peak detection algorithm.

In an embodiment, each of the plurality of pressure sensor corresponds to the plurality of pressure points in the foot of the subject, and each pressure point corresponds to the node in the connectivity graph. Each line connecting two adjacent nodes forms an edge of the graph. Here the graph G is defined as G(V,E) where, V is a set of vertices (nodes) and E is a set of edges, N (N=|V|) is the number of nodes and M (M=|E|) is the number of edges. For brevity of description the vertex can be alternatively called as node. For brevity of description, the graph can be alternatively called as the connectivity graph.

In an embodiment, the graph is generated using 100 consecutive stride information for left foot of each of the subject. Further, Performance of the connectivity graph depends on a sparsity value associated with the connectivity graph. In an embodiment, the sparsity value is selected as the largest possible threshold so that all nodes in the connectivity graph are connected at least to another node in the connectivity graph. In another embodiment, a plurality of connectivity graphs are generated for each subject by varying the sparsity value between 0 to 1 in steps of 0.1.

Figure 4A:
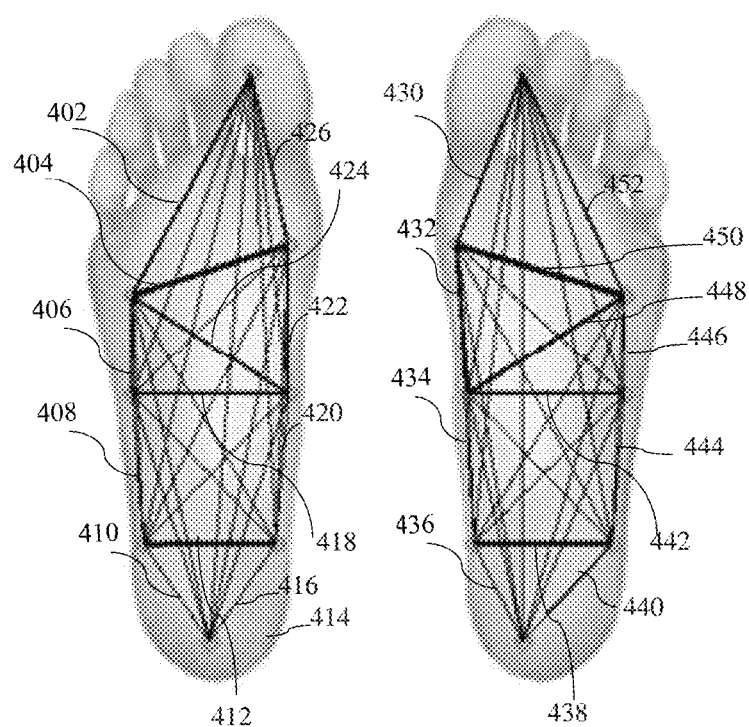
FIG. 4A is an exemplary diagram illustrating a connectivity graph of a control subject, accordance with some embodiments of the present disclosure.
Figure 4B:
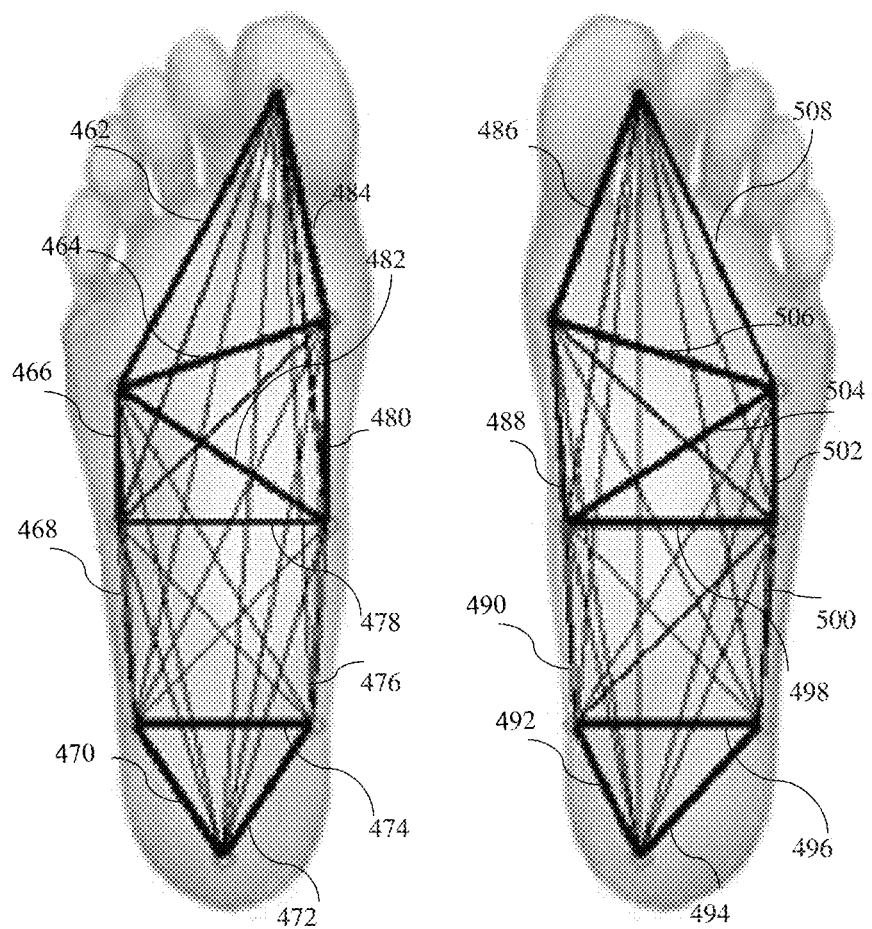
FIG. 4B is an exemplary diagram illustrating a connectivity graph of a Parkinson's disease subject, accordance with some embodiments of the present disclosure.

FIG. 4A is an exemplary diagram illustrating the connectivity graph of the control subject, accordance with some embodiments of the present disclosure. FIG. 4B is an exemplary diagram illustrating the connectivity graph of the Parkinson's disease subject, accordance with some embodiments of the present disclosure. Referring to FIG. 4A and FIG. 4B, density of edges is more in Parkinson's disease subject than the control subject. A plurality of edges 462, 464, 466, 468, 470, 472, 474, 476, 478, 480, 482, 484, 486, 488, 490, 492, 494, 496, 498, 500, 502, 504, 506 and 508 as shown in FIG. 4B are thicker than the plurality of edges 420, 404, 406, 408, 410, 412, 414, 416, 418, 420, 422, 424, 426, 430, 432, 434, 436, 438, 440, 442, 444, 446, 448, 450, and 452 as shown in FIG. 4A. The thickness associated with the edges of the connectivity graph of the Parkinson's disease subject illustrates that the Parkinson's disease subject gives more pressure on the edges of the foot.

Further, the gait dynamics analysis unit 250 of the system 200 can be configured to calculate the mediolateral stability index from the calculated stride information associated with each node in the connectivity graph based on the betweenness centrality associated with each node. The method of calculating the mediolateral stability index from the stride information associated with each node of the connectivity graph based on the betweenness centrality associated with each node includes (i) calculating, a Pearson's correlation coefficient associated with each edge from the plurality of edges based on the stride information associated with two adjacent nodes connected by each edge (ii) Constructing, a weighted adjacency matrix from the connectivity graph based on the Pearson's correlation coefficient associated with each edge from the plurality of edges (iii) Calculating, a total number of shortest paths from a source node to a sink node by utilizing the weighted adjacency matrix (iv) Calculating, for each node, a number of shortest paths from the source node to the sink node passing through each node by utilizing the weighted adjacency matrix. In an embodiment, referring to FIG. 5, the source node can be node 1 and the sink node can be node 8. In another embodiment, the source node can be node 8 and the sink node can be node 1 (v) Calculating, a betweenness centrality for each node excluding the source node and the sink node by dividing the number of shortest paths from the source node to the sink node passing through each node by the total number of shortest paths from the source node to the sink node and (vi) Calculating, a mediolateral stability index from the betweenness centrality associated with each node based on a difference between the betweenness centrality associated with each node and a set of adjacent nodes associated with each node.

In an embodiment, the betweenness centrality is utilized to measure an influence associated with a given node over the flow of information between all other nodes in the connectivity graph. The betweenness centrality associated with each node is calculated by utilizing the equation 1.

$$B_i = \Sigma_{m \neq i \neq n \in G} \frac{\sigma_{mn}(i)}{\sigma_{mn}} \quad (1)$$

Here, $\sigma_{mn}(i)$ is the number of shortest paths from node 'm' to node 'n' that passes through node 'i' and $\sigma_{mn}$ is the total number of shortest paths from node 'm' to node 'n'. The betweenness centrality includes information of one pressure point in association with all other pressure points.

Figure 5:
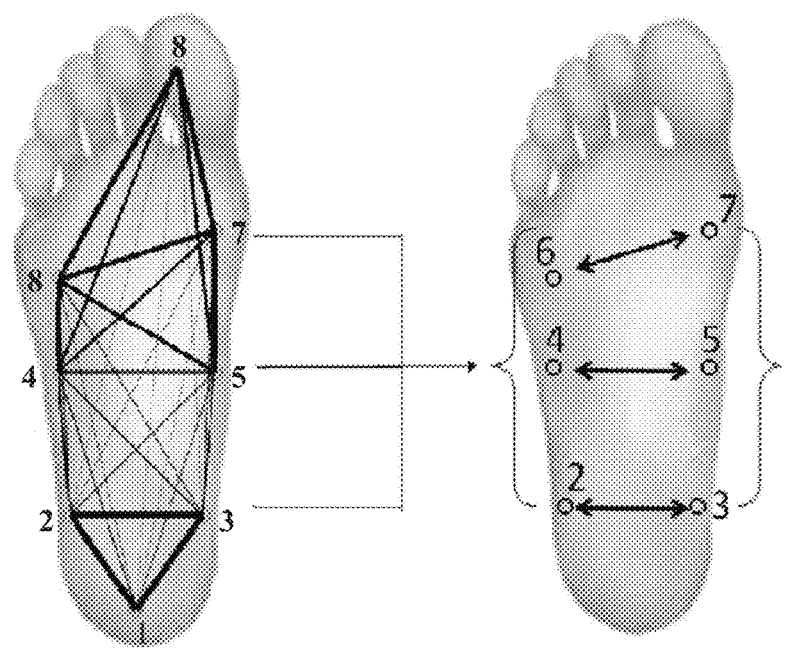
FIG. 5 is an exemplary diagram illustrating three pairs of adjacent pressure points from the connectivity graph utilized for calculating a mediolateral stability index, accordance with some embodiments of the present disclosure.

In an embodiment, a plurality of node pairs are selected for calculating the mediolateral stability index. Here, the plurality of node pairs includes node pair (2,3), node pair (4,5) and node pair (6,7) as shown in FIG. 5. The mediolateral stability index associated with the node pair (2,3) is calculated using the equation 2. Here, the betweenness centrality of the node 3 is subtracted from the betweenness centrality of the node 2 to obtain the mediolateral stability index of the node pair (2,3). Similarly, the mediolateral stability index associated with the node pair (4,5) is calculated using the equation 3. Here, the betweenness centrality of the node 5 is subtracted from the betweenness centrality of the node 4 to obtain the mediolateral stability index of the node pair (4,5). The mediolateral stability index associated with the node pair (6,7) is calculated using the equation 4. Here, the betweenness centrality of the node 7 is subtracted from the betweenness centrality of the node 6 to obtain the mediolateral stability index of the node pair (6,7).

$$MLS_{2\text{-}3} = |B_2 - B_3| \quad (2)$$

$$MLS_{4\text{-}5} = |B_4 - B_5| \quad (3)$$

$$MLS_{6\text{-}7} = |B_6 - B_7| \quad (4)$$

Further, the gait dynamics analysis unit 250 of the system 200 can be configured to detect an intensity of the Parkinson's disease of the subject by comparing the mediolateral stability index with a predetermined value. Here, the intensity of the Parkinson's disease of the subject is classified into one of no Parkinson's disease, mild Parkinson's disease, moderate Parkinson's disease and severe Parkinson's disease. The predetermined value is calculated based on a plurality of graph metrics. The method of calculating the plurality of graph metrics is described below.

In an embodiment, the plurality of graph metrics includes Clustering Coefficient (CC), Modularity (M), Characteristic Path Length (CPL), Local Efficiency (LE) and Link Density (LD) for the control group (CO) and Parkinson's disease (PD) group by utilizing the sparsity value of 0.3.

In an embodiment, calculating the modularity of the graph provides a group of structurally or functionally associated nodes. Alternatively, modularity is a statistic to quantify a degree to which the network can be subdivided into clearly delineated groups. The modularity is measured by the equation 5.

$$Q = \frac{1}{2m}\Sigma_{ij}\left[A_{ij} - \frac{K_i K_j}{2m}\right]\delta(C_i, C_j) \quad (5)$$

Here, $A_{ij}$ is a weight associated with an edge between a node T and a node 'j'. $K_i$ is a sum of weights of the edges attached to the node 'i' and $K_j$ is a sum of weights of the edges attached to the node 'j'. 'm' is the sum of all of the edge weights of the graph. $C_i$, $C_j$ are the group of the nodes and $\delta$ is a simple delta function.

Link density (LD) of the graph is measured by the equation 6.

$$num_{nodes}(num_{nodes}-1)/2 \quad (6)$$

where $num_{nodes}$ is the maximum number of nodes in the graph. If the LD value is high, the density of the graph is more. The variation in LD is more for the control subjects and the Parkinson's disease subjects, for example $p<0.05$. Further, the mean LD is higher in Parkinson's disease subject and the foot of the Parkinson's disease subject appears to be flat, and hence there exists strong links between the pressure points as shown in FIGS. 4A and 4B.

Efficiency: Global efficiency and local efficiency measures the ability of a network to transmit information at the global and local level. For the graph G(V, E), the global efficiency is given by the equation 7.

$$E_{glob}(G) = \frac{1}{N(N-1)}\Sigma_{i\in G j\in G, i\neq j}\frac{1}{d_{ij}} \quad (7)$$

Where, $d_{ij}$ is the shortest path length between the node 'i' and the node 'j' in G. The global efficiency of G is given by the equation 8.

$$E_{glob}(G) = \frac{1}{N}\sum_{i\in G} E_{glob}(G_i) \quad (8)$$

Where, $E_{glob}(G)$ is the global efficiency of $G_i$, wherein $G_i$ is a subgraph obtained from a plurality of neighbors associated with the node 'i'.

The clustering coefficient $C_i$ of a node 'i' is given by the equation 9.

$$C_i = \frac{2T}{d_i}(d_i - 1) \quad (9)$$

Here, T indicates a number existing connections among the neighbors of 'i' and $d_i$ is a degree associated with the node 'i'.

Table 1 below provides a comparison of the plurality of graph metrics between left legs in CO subject and Parkinson's disease (PD) subject.

TABLE 1

|     | Average CO (left foot) | Average PD (left foot) | p-value |
| --- | --- | --- | --- |
| M   | 0.375483 | 0.304818 | 0.005468 |
| LD  | 0.366093 | 0.417035 | 0.001904 |
| CpI | 328.9 | 462.01 | 0.000408 |
| CC  | 0.6 | 0.69 | 0.003 |
| LE  | 0.340 | 0.830 | 0.002 |

As depicted in the table 1, the calculated plurality of graph metrics for Parkinson's disease (PD) and Control group (CO) is given. The plurality of graph metrics, except 'Modularity' provides statistically significant result at the selected sparsity value of 0.3. However, in between PD group, that is the 'Mild' and 'Moderate' or 'Control' and 'Mild' group, no statistically significant results were obtained. Also, physical significance of conventional graph metric values are difficult to interpret in this scenario. Conventional graph theoretic features can differentiate between control and PD group, but cannot differentiate between stages of PD or neither can evaluate early detection or quantify disease progression.

In an embodiment, the mediolateral stability index based categorization of the subjects is as shown in Table 2A. Table 2B and Table 2C. As depicted in Tables 2A, 2B and 2C, the calculated mediolateral stability index is utilized for a plurality of categorization including the control subject and the Parkinson Disease (PD) subject, the control subject and the Mild PD subject and the Mild PD subject and the moderate PD subject. For differentiating between the control subject and PD subject, all the node pair shows statistically significant result. For early screening, the Control subject and the Mild PD subject, the node pairs (4, 5) and (6, 7) provides statistically significant result. For early screening, the Mild PD subject and Moderate PD subject, the node pairs (4, 5) and (6, 7) provides statistically significant result.

TABLE 2A

| Node Pair | MLSI for Control subject | MLSI for PD subject | P value (accuracy) (<0.05) |
| --- | --- | --- | --- |
| 2-3 | 1.21 | 5.7 | 0.0431* |
| 4-5 | 3.35 | 9.1 | 0.021* |
| 6-7 | 0.41 | 2.9 | 0.013* |

TABLE 2B

| Node Pair | MLSI for Control subject | MLSI for Mild PD subject | P value |
| --- | --- | --- | --- |
| 2-3 | 4.03 | 1.6 | 0.021* |
| 4-5 | 8.4 | 5.1 | 0.045* |
| 6-7 | 0.21 | 0.22 | 0.073 |

TABLE 2C

| Node Pair | MLSI for Mild PD subject | MLSI for Moderate PD subject | P value |
| --- | --- | --- | --- |
| 2-3 | 1.63 | 4.1 | 0.023* |
| 4-5 | 4.8 | 7.2 | 0.113* |
| 6-7 | 0.2 | 1.1 | 0.052 |

The table 2 indicated that, the MLS metric effectively distinguishes Control, Mild and Moderate group and also indicates that as PD progresses, abrupt and chaotic behavior are most likely to occur in the upper quadrant of foot, precisely the area between (4, 5) and (6, 7) node pairs (pressure zone). The '*' in the table indicates that the p value is less than 0.05 and when the p value is less than 0.05, the differentiation between the control subject and PD subject, the control subject and the mild PD subject, the control subject and the moderate PD subject is clear.

In an embodiment, the category of the subject obtained by the present disclosure is compared with a Hoehn and Yahr (HY) scale to test the efficiency of the present disclosure. The present disclosure is providing results equivalent to the HY scale. Moreover, the present disclosure provides more categories including 'mild Parkinson's disease' and 'moderate Parkinson's disease' which are not available in the HY scale. The HY scale is a standard manual calculation method used for detecting the Parkinson's disease. For example, a progression of the Parkinson's disease is identified in the range of 0 to 5 in HY scale, wherein 0 in the HY scale indicates that there is 'no' Parkinson's disease, 2 in the HY scale indicates 'mild' Parkinson's disease, the value between 2 and 5 in the Hy scale indicates 'moderate' Parkinson's disease and 5 in the HY scale indicates that the Parkinson's disease is 'severe'.

Figure 6A:
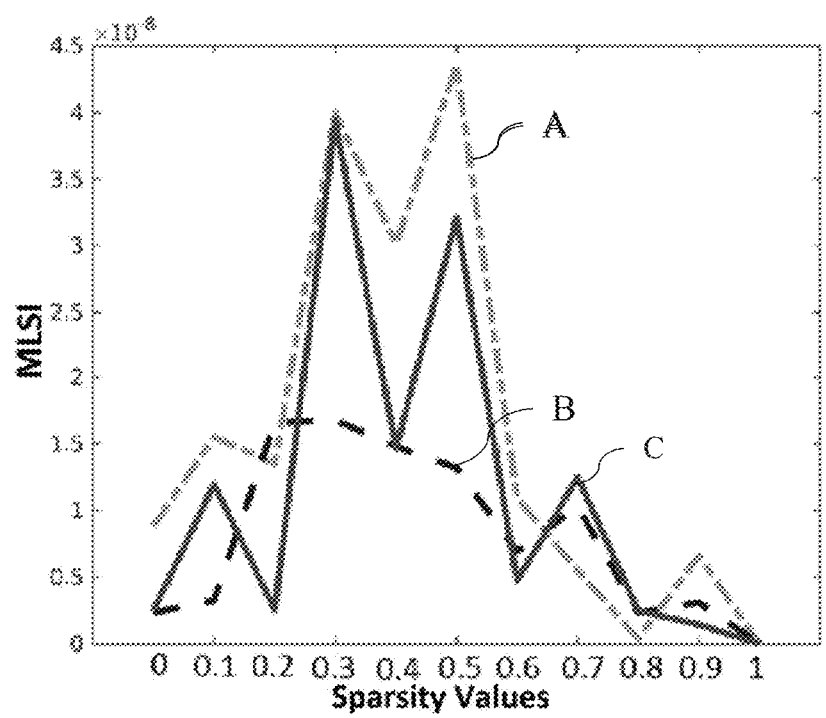
FIGS. 6A, 6B and 6C are exemplary graphs illustrating variation of the mediolateral stability index corresponding to a plurality of sparsity values for three pair of pressure points across the control subject, a mild Parkinson's disease subject and a moderate Parkinson's disease subject, in accordance with some embodiments of the present disclosure.
Figure 6B:
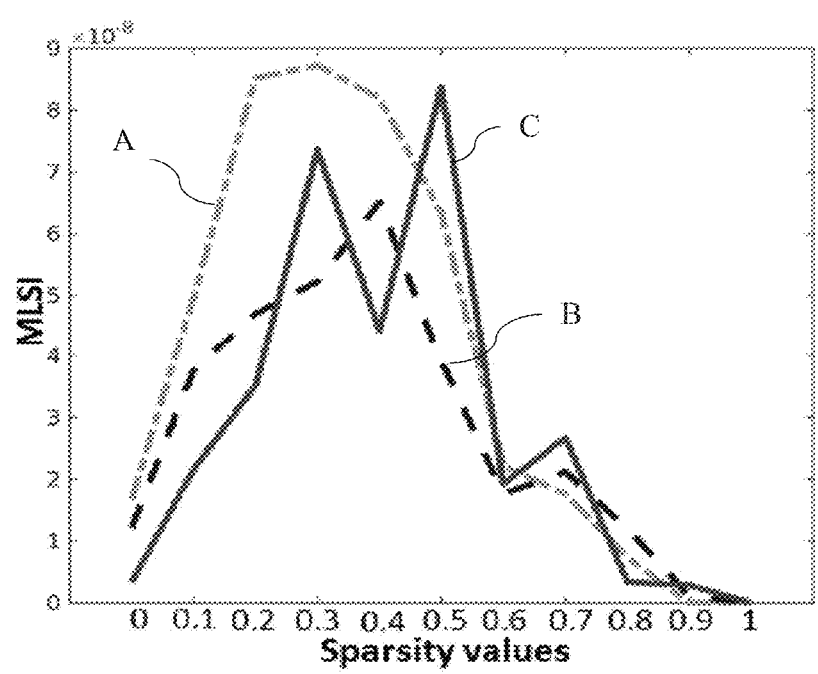
Figure 6C:
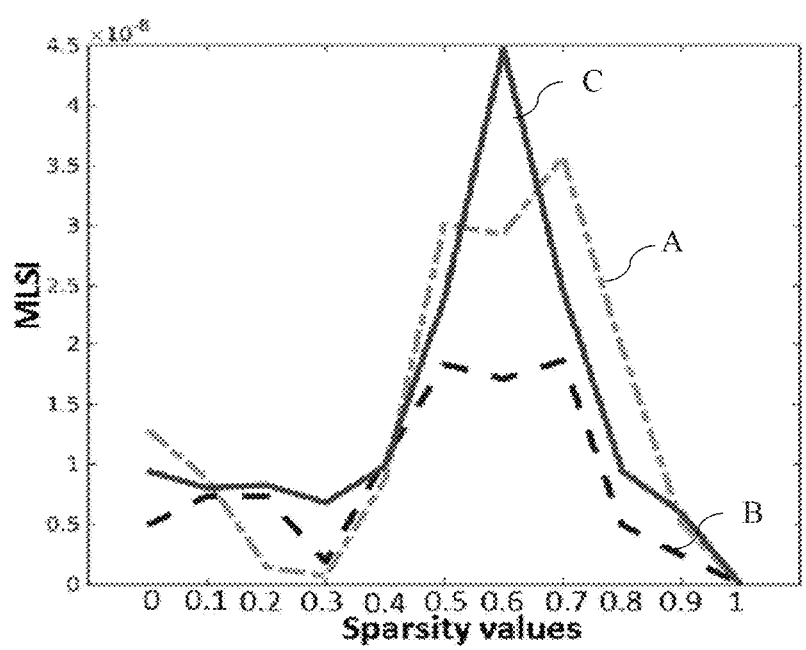

FIGS. 6A, 6B and 6C are exemplary graphs illustrating variation of the mediolateral stability index (MLSI) corresponding to a plurality of sparsity values for three pair of pressure points across the control subject, a mild Parkinson's disease subject and a moderate Parkinson's disease subject, in accordance with some embodiments of the present disclosure. Here, a variation of the mediolateral stability index corresponding to the plurality of sparsity values of the Control subject is plotted as A. The variation of the mediolateral stability index corresponding to the plurality of sparsity values of the mild Parkinson's disease subject is plotted as B. The variation of the mediolateral stability index corresponding to the plurality of sparsity values of the moderate Parkinson's disease subject is plotted as C. Here, the sparsity value is varied from 0 to 1. Referring to FIG. 6A, the variation of the mediolateral stability index corresponding to the plurality of sparsity value for the node pair (2,3) is plotted for the control subject, the mild Parkinson's disease subject and the moderate Parkinson's disease subject. Referring to FIG. 6B, the variation of the mediolateral stability index corresponding to the plurality of sparsity value for the node pair (4,5) is plotted for the control subject, the mild Parkinson's disease subject and the moderate Parkinson's disease subject. Referring to FIG. 6C, the variation of the mediolateral stability index corresponding to the plurality of sparsity value for the node pair (6,7) is plotted for the control subject, the mild Parkinson's disease subject and the moderate Parkinson's disease subject. In an embodiment, the sparsity value of 0.3 provides statistically significant result.

Figure 7:
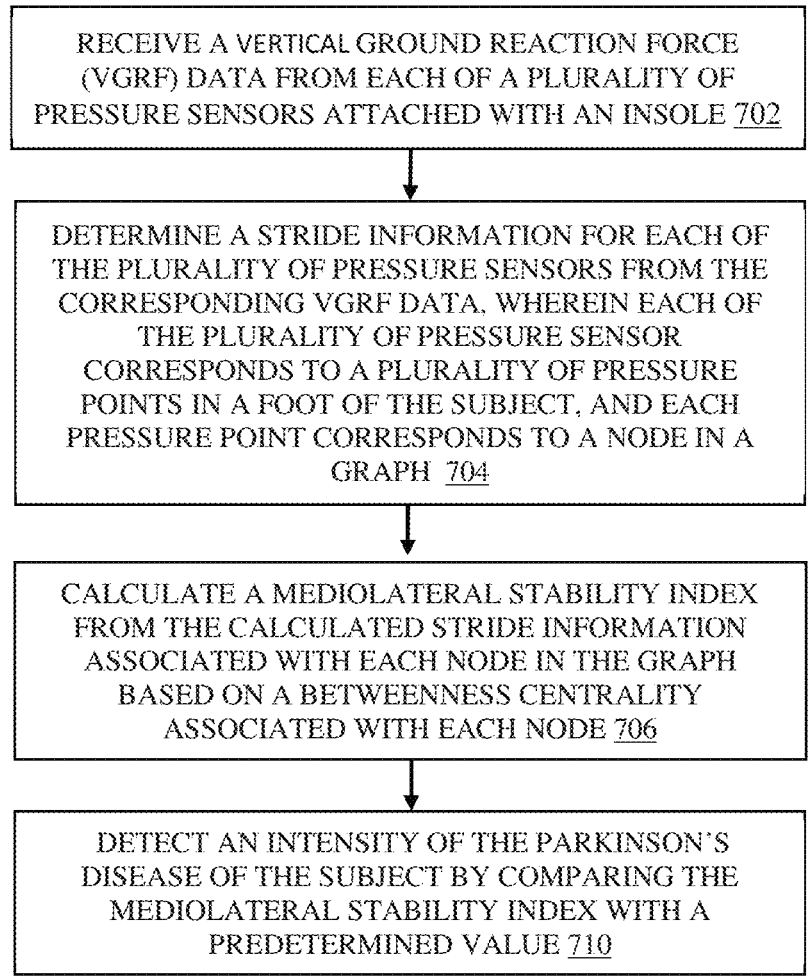
FIG. 7 is a flow diagram illustrating a method for detecting a Parkinson's disease progression of the subject, in accordance with some embodiments of the present disclosure

FIG. 7 illustrates a flow diagram for the method 700 for detecting Parkinson's disease, according to some embodiments of the present disclosure. The method 700 may be described in the general context of computer executable instructions. Generally, computer executable instructions can include routines, programs, objects, components, data structures, procedures, modules, functions, etc., that perform particular functions or implement particular abstract data types. The method 700 may also be practiced in a distributed computing environment where functions are performed by remote processing devices that are linked through a communication network. The order in which the method 700 is described is not intended to be construed as a limitation, and any number of the described method blocks can be combined in any order to implement the method 700, or an alternative method. Furthermore, the method 700 can be implemented in any suitable hardware, software, firmware, or combination thereof.

FIG. 7 is a flow diagram illustrating a method 700 for detecting Parkinson's disease progression of the subject, in accordance with some embodiments of the present disclosure. At 702, the system 200 receives, by a one or more hardware processors, the Vertical Ground Reaction Force (VGRF) data from each of the plurality of pressure sensors attached to the insole. At 704, the system 200 determines, by the one or more hardware processors, the stride information for each of the plurality of pressure sensors from the corresponding VGRF data, wherein each of the plurality of pressure sensors correspond to a plurality of pressure points in the foot of the subject, and each pressure point corresponds to a node in the connectivity graph. At 706, the system 200 calculates by the one or more hardware processors, the mediolateral stability index from the calculated stride information associated with each node in the connectivity graph based on the betweenness centrality associated with each node. At 708, the system 200 detects by the one or more hardware processors, the intensity of the Parkinson's disease of the subject by comparing the mediolateral stability index with a predetermined value.

Figure 8:
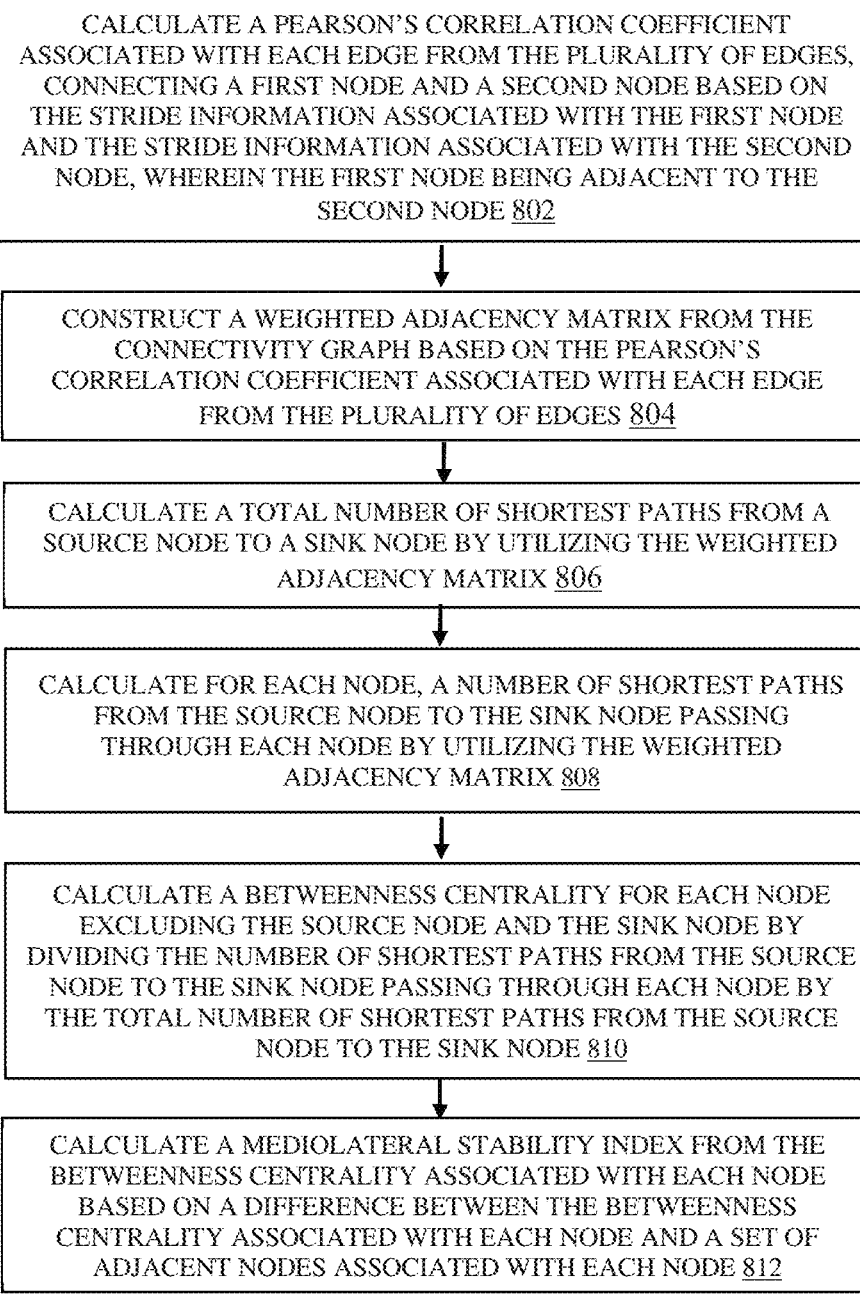
FIG. 8 is a flow diagram illustrating a method of calculating the mediolateral stability index from the calculated stride information associated with each node in the graph based on the betweenness centrality associated with each node, in accordance with some embodiments of the present disclosure.

FIG. 8 is a flow diagram illustrating a method of calculating the mediolateral stability index from the calculated stride information associated with each node in the graph based on the betweenness centrality associated with each node, in accordance with some embodiments of the present disclosure. At step 802, the Pearson's correlation coefficient associated with each edge from the plurality of edges is calculated. Here, two adjacent nodes are connected by an edge and the Pearson correlation coefficient of edge is calculated based on the stride information associated with the adjacent nodes connected by the edge. At step 804, the weighted adjacency matrix is constructed from the connectivity graph based on the Pearson's correlation coefficient associated with each edge from the plurality of edges. At step 806, a total number of shortest paths from a source node to a sink node is calculated by utilizing the weighted adjacency matrix. At step 808, for each node, a number of shortest paths from the source node to the sink node passing through each node is calculated by utilizing the weighted adjacency matrix. At step 810, a betweenness centrality is calculated for each node excluding the source node and the sink node by dividing the number of shortest paths from the source node to the sink node passing through each node by the total number of shortest paths from the source node to the sink node. At step 812, the mediolateral stability index is calculated from the betweenness centrality associated with each node based on a difference between the betweenness centrality associated with each node and a set of adjacent nodes of each node.

Experimentation: In an embodiment, the data set used for experimentation includes a set of Vertical Ground Reaction Force (VGRF) data of 93 subjects with idiopathic Parkinson's disease (mean age: 66.3 years) with moderate disease severity and 73 control subjects. The control subjects were free from any neurological or gait related disorders. All the subjects with Parkinson's disease had mild to moderate Parkinson's disease, as concluded from Hoehn-Yahr (HY) scale (value between 2 to 3). The subjects were asked to walk for a distance of 100 m in their self-selected speed, wearing an instrumented shoe, fitted with insole sensors at dedicated pressure points. There are 16 sensors in total, 8 for each foot. The sensors measured VGRF data under the foot at the point of placement. Data were acquired at 100 Hz sampling frequency. The VGRF data were filtered to reduce spurious noise and suppress raw signal readout below 20 N and the VGRF data collected during the first 20 seconds of the plurality of pressure sensors were discarded. Further the VGRF data is weight normalized using the demographic information given in the database.

In an embodiment, human gait cycle includes a periodic stance and swing pattern and the human gait cycle is processed to extract stride information. A stride cycle is the period of time during which a foot touches the ground known as heel strike phase, goes off the ground (toe off phase), and again makes contact with the ground. Maximum VGRF is calculated as the mean of maximum value in each stride for total 35 strides of both legs of each subject, considering all 8 sensors for each foot. Average of maximum VGRF reported by the 8 pressure sensors is calculated for 35 consecutive strides.

In an embodiment, to compensate postural imbalance, PD subjects shows higher relative load in the forefoot regions, resulting in flat-foot gait. Results obtained from the experimentation indicates a characteristic flat footedness for PD groups. As PD progresses, calculated MLS index shows more prominence in the forefoot region. The Medial load shifting bias or a change in load distribution and its fluctuations in PD subjects as PD progresses reflects the differential dynamics of PD gait.

In an embodiment, the calculated MLS metric incorporates the hidden dynamism in the medial load distribution pattern and its changes as PD progresses. The present disclosure along with traditional gait variables like stride time, swing time variability, can be used to augment the accuracy of the disease severity estimation. The mediolateral stability index metric along with the insole can serve as an indicator for medication dose adjustment as per the activity and stability of the specific subject, monitored through the insole combined with smart phone application.

In an embodiment, a step by step procedure to calculate the mediolateral stability index is as provided in example code below:

```
1:   procedure VGRF SIGNAL ACQUISITION (ch1 to ch8)
2:     for i = 1 : nChannels do
3:       datai = VGRF data of channel i
4:     end for
       return data
5:   end procedure
6:   procedure CORRELATION MATRIX CREATION(data)
7:     for i = 1 : nChannels do
8:       for j = 1 : nChannels do
9:         if i == j then
              M [i,j] = 0  //self connecting nodes
11:        else
12:          x = data_i
13:          y = data_j
14:
```

$$M[i, j] = \frac{\Sigma(x - \bar{x}) * (y - \bar{y})}{\sqrt{\Sigma(x - \bar{x})^2 * \Sigma(y - \bar{y})^2}}$$

```
15:        end if
16:      end for
17:    end for . where x̄ and ȳ are the means of x and y
       respectively.
       return M
18:  end procedure
19:  procedure NETWORK CREATION(M)
20:    thresholds = [0, ....., 0:9]
21:    nThresholds = number of thresholds
22:    for k = 1 : nThresholds do
23:      t = thresholds[k]
24:      for i = 1 : nChannels do
25:        for j = 1 : nChannels do
26:          if M [i, j] ≥ t then
27:            N_k[i,j] = 1
28:          else
29:            N_k[i,j] = 0
30:          end if
31:        end for
32:      end for
33:    end for
       return N
34:  end procedure
35:  procedure CALCULATE BETWEENNESS INDEX
36:
```

$$B_i = \Sigma_{m \neq i \neq n \in G} \frac{\sigma_{mn}(i)}{\sigma_{mn}}$$

```
37:  end procedure
38:  procedure CALCULATE MEDIOLATERAL STABILITY INDEX
39:    MLS_{i-j} = |B_i - B_j|. i, j are adjacent pressure points
40:  end procedure
```

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein addresses unresolved problem of identifying biomarkers for detecting progression of Parkinson's disease. The embodiment, thus provides graph connectivity approach to derive a novel metric associated with changes in mediolateral pressure distribution based on the VGRF data obtained from the insole. Further, the mediolateral stability index is utilized as a screening index to measure flat footedness of the subject. Moreover, the embodiments herein further provides, a monitoring system for Parkinson's disease.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor implemented method for detecting Parkinson's disease progression of a subject, the method comprising:
   receiving, by a one or more hardware processors, a Vertical Ground Reaction Force (VGRF) data from each of a plurality of pressure sensors attached to an insole, wherein the VGRF data during first 20 seconds of each of the plurality of pressure sensors is discarded, and wherein the VGRF data is weight normalized using demographic information stored in a database;
   determining, by the one or more hardware processors, a stride information for each of the plurality of pressure sensors from the corresponding VGRF data, wherein each of the plurality of pressure sensors correspond to a plurality of pressure points in a foot of the subject, and each pressure point corresponds to a node in a graph, wherein the plurality of pressure points in the foot corresponding to the plurality of pressure sensors are represented in an arbitrary reference coordinate system, and wherein an arbitrary axis in the arbitrary reference coordinate system is placed such that a left foot is positioned on a positive axis, a right foot is positioned on a negative axis, an upper half section of the left foot and the right foot are positioned on the positive axis and a lower half of the left foot and the right foot are positioned on the negative axis;
   calculating, by the one or more hardware processors, a mediolateral stability index from the calculated stride information associated with each node in the graph based on a betweenness centrality associated with each node, wherein the mediolateral stability index is utilized as a screening index to measure flat footedness of the subject, wherein the mediolateral stability index is associated with changes in mediolateral pressure distribution based on the VGRF data received from the insole, wherein the mediolateral stability index incorporates hidden dynamism in medial load distribution pattern and the mediolateral stability index changes as the Parkinson's disease progresses, wherein the betweenness centrality is utilized to measure an influence associated with a node over the flow of information between all other nodes in the graph, wherein the betweenness centrality includes information of one pressure point in association with all other pressure points, and wherein the step of calculating the mediolateral stability index from the calculated stride information associated with the each node in the graph based on the betweenness centrality associated with the each node comprises:
      calculating, a Pearson's correlation coefficient associated with each edge from a plurality of edges, connecting a first node and a second node based on the stride information associated with the first node and the stride information associated with the second node, wherein the first node is adjacent to the second node;
      constructing, a weighted adjacency matrix from the graph based on the Pearson's correlation coefficient associated with each edge from the plurality of edges;

calculating, a total number of shortest paths from a source node to a sink node by utilizing the weighted adjacency matrix;

calculating, for each node, a number of shortest paths from the source node to the sink node passing through each node by utilizing the weighted adjacency matrix;

calculating, the betweenness centrality for each node excluding the source node and the sink node by dividing the number of shortest paths from the source node to the sink node passing through each node by the total number of shortest paths from the source node to the sink node; and calculating, the mediolateral stability index from the betweenness centrality associated with each node based on a difference between the betweenness centrality associated with each node and a set of adjacent nodes associated with each node; and detecting, by the one or more hardware processors, an intensity of the Parkinson's disease of the subject by comparing the mediolateral stability index with a predetermined value.

2. The processor implemented method of claim 1, wherein intensity of the Parkinson's disease of the subject is classified into one of no Parkinson's disease, mild Parkinson's disease, moderate Parkinson's disease and severe Parkinson's disease.

3. A system for detecting Parkinson's disease progression of a subject, the system comprising:

an insole with a plurality of pressure sensors;
at least one memory storing programmed instructions;
at least one hardware processor operatively coupled to the at least one memory, wherein the at least one hardware processor are configured by the programmed instruction to:

receive, a Vertical Ground Reaction Force (VGRF) data from each of a plurality of pressure sensors attached to an insole, wherein the VGRF data during first 20 seconds of each of the plurality of pressure sensors is discarded, and wherein the VGRF data is weight normalized using demographic information stored in a database;

determine, a stride information for each of the plurality of pressure sensors from the corresponding VGRF data, wherein each of the plurality of pressure sensors correspond to a plurality of pressure points in a foot of the subject, and each pressure point corresponds to a node in a graph, wherein the plurality of pressure points in the foot corresponding to the plurality of pressure sensors are represented in an arbitrary reference coordinate system, and wherein an arbitrary axis in the arbitrary reference coordinate system is placed such that a left foot is positioned on a positive axis, a right foot is positioned on a negative axis, an upper half section of the left foot and the right foot are positioned on the positive axis and a lower half of the left foot and the right foot are positioned on the negative axis;

calculate, a mediolateral stability index from the calculated stride information associated with each node in the graph based on a betweenness centrality associated with each node, wherein the mediolateral stability index is utilized as a screening index to measure flat footedness of the subject, wherein the mediolateral stability index is associated with changes in mediolateral pressure distribution based on the VGRF data received from the insole, wherein the mediolateral stability index incorporates hidden dynamism in medial load distribution pattern and the mediolateral stability index changes as the Parkinson's disease progresses, wherein the betweenness centrality is utilized to measure an influence associated with a node over the flow of information between all other nodes in the graph, wherein the betweenness centrality includes information of one pressure point in association with all other pressure points, and wherein calculating the mediolateral stability index from the calculated stride information associated with the each node in the graph based on the betweenness centrality associated with the each node comprises:

calculating, a Pearson's correlation coefficient associated with each edge from a plurality of edges, connecting a first node and a second node based on the stride information associated with the first node and the stride information associated with the second node, wherein the first node is adjacent to the second node;

constructing, a weighted adjacency matrix from the graph based on the Pearson's correlation coefficient associated with each edge from the plurality of edges;

calculating, a total number of shortest paths from a source node to a sink node by utilizing the weighted adjacency matrix;

calculating, for each node, a number of shortest paths from the source node to the sink node passing through each node by utilizing the weighted adjacency matrix;

calculating, the betweenness centrality for each node excluding the source node and the sink node by dividing the number of shortest paths from the source node to the sink node passing through each node by the total number of shortest paths from the source node to the sink node; and calculating, the mediolateral stability index from the betweenness centrality associated with each node based on a difference between the betweenness centrality associated with each node and a set of adjacent nodes associated with each node;

detect, an intensity of the Parkinson's disease of the subject by comparing the mediolateral stability index with a predetermined value.

4. The system of claim 3, wherein intensity of the Parkinson's disease of the subject is classified into one of no Parkinson's disease, mild Parkinson's disease, moderate Parkinson's disease and severe Parkinson's disease.

5. One or more non-transitory machine readable information storage mediums comprising one or more instructions which when executed by one or more hardware processors causes:

receiving, by a one or more hardware processors, a Vertical Ground Reaction Force (VGRF) data from each of a plurality of pressure sensors attached to an insole, wherein the VGRF data during first 20 seconds of each of the plurality of pressure sensors is discarded, and wherein the VGRF data is weight normalized using demographic information stored in a database;

determining, by the one or more hardware processors, a stride information for each of the plurality of pressure sensors from the corresponding VGRF data, wherein each of the plurality of pressure sensors correspond to a plurality of pressure points in a foot of the subject, and each pressure point corresponds to a node in a graph, wherein the plurality of pressure points in the foot corresponding to the plurality of pressure sensors are represented in an arbitrary reference coordinate system, and wherein an arbitrary axis in the arbitrary reference coordinate system is placed such that a left foot is positioned on a positive axis, a right foot is positioned on a negative axis, an upper half section of the left foot and the right foot are positioned on the positive axis and a lower half of the left foot and the right foot are positioned on the negative axis;

calculating, by the one or more hardware processors, a mediolateral stability index from the calculated stride information associated with each node in the graph based on a betweenness centrality associated with each node, wherein the mediolateral stability index is utilized as a screening index to measure flat footedness of the subject, wherein the mediolateral stability index is associated with changes in mediolateral pressure distribution based on the VGRF data received from the insole, wherein the mediolateral stability index incorporates hidden dynamism in medial load distribution pattern and the mediolateral stability index changes as the Parkinson's disease progresses, wherein the betweenness centrality is utilized to measure an influence associated with a node over the flow of information between all other nodes in the graph, wherein the betweenness centrality includes information of one pressure point in association with all other pressure points, and wherein the step of calculating the mediolateral stability index from the calculated stride information associated with the each node in the graph based on the betweenness centrality associated with the each node comprises:

calculating, a Pearson's correlation coefficient associated with each edge from a plurality of edges, connecting a first node and a second node based on the stride information associated with the first node and the stride information associated with the second node, wherein the first node is adjacent to the second node;

constructing, a weighted adjacency matrix from the graph based on the Pearson's correlation coefficient associated with each edge from the plurality of edges;

calculating, a total number of shortest paths from a source node to a sink node by utilizing the weighted adjacency matrix;

calculating, for each node, a number of shortest paths from the source node to the sink node passing through each node by utilizing the weighted adjacency matrix;

calculating, the betweenness centrality for each node excluding the source node and the sink node by dividing the number of shortest paths from the source node to the sink node passing through each node by the total number of shortest paths from the source node to the sink node; and calculating, the mediolateral stability index from the betweenness centrality associated with each node based on a difference between the betweenness centrality associated with each node and a set of adjacent nodes associated with each node; and detecting, by the one or more hardware processors, an intensity of the Parkinson's disease of the subject by comparing the mediolateral stability index with a predetermined value.

* * * * *